United States Patent [19]

Keyworth

[11] Patent Number: 4,579,990

[45] Date of Patent: Apr. 1, 1986

[54] PROCESS FOR THE OLIGOMERIZATION OF PROPYLENE

[75] Inventor: Donald A. Keyworth, Houston, Tex.

[73] Assignee: Tenneco Oil Company, Houston, Tex.

[21] Appl. No.: 754,763

[22] Filed: Jul. 15, 1985

[51] Int. Cl.$^4$ ................................................ C07C 2/28
[52] U.S. Cl. .................... 585/510; 585/515; 585/526
[58] Field of Search ............... 585/510, 515, 520, 521, 585/526

[56] References Cited

U.S. PATENT DOCUMENTS

| | | | |
|---|---|---|---|
| 4,242,530 | 12/1980 | Smith, Jr. | 585/510 |
| 4,301,315 | 11/1981 | Haskell et al. | 585/510 |
| 4,313,016 | 1/1982 | Manning | 585/515 |
| 4,375,576 | 3/1983 | Smith, Jr. | 585/515 |
| 4,400,565 | 8/1983 | Darden et al. | 585/510 |
| 4,463,211 | 7/1984 | Manning | 585/515 |
| 4,482,775 | 11/1984 | Smith, Jr. | 585/510 |

FOREIGN PATENT DOCUMENTS 0214604  10/1984  German Democratic Rep. ................ 585/510

Primary Examiner—John Doll
Assistant Examiner—A. Pal
Attorney, Agent, or Firm—Kenneth H. Johnson

[57] ABSTRACT

Propylene contained in mixed $C_3/C_4$ streams containing at least 5 wt. % isobutene, for example, catalytic cracker offgas, may be recovered as a useful gasoline component by oligomerizing the propylene in liquid phase at 80° to 130° C. at LHSV 2 to 5 in the presence of an acidic cation exchange resin whereby the oligomers produced are primary $C_6$ to $C_8$ mono olefins.

12 Claims, No Drawings

PROCESS FOR THE OLIGOMERIZATION OF PROPYLENE

BACKGROUND OF THE INVENTION

1. Field of the Invention

The present invention relates to oligomerization, particularly dimerization, of propylene in streams containing $C_3$ and $C_4$ alkenes using acid cation exchange resin catalyst.

2. Related Art

Refinery streams such as catalytic cracker offgas often contain large quantities of propylene in a mixture with various $C_4$'s (n-butene, isobutene, n-butane and isobutane). There has been a great deal of research directed to recovering the $C_4$'s, e.g., by etherification, fractionation and oligomerization using acid cation exchange resins, however, the $C_3$'s which include propylene have generally been treated as inerts, in the same manner as isobutane and n-butane in these recoveries.

The reaction of olefins, including propylene to produce long chain polymers, using certain organo-metallic catalysts is well known. The best known catalysts are homogeneous catalysts consisting of compounds of metals of groups II to VI of the Periodic Table of Elements in combination with other compounds of metals of groups I to III, such as the Ziegler catalysts, which are preferably specific combinations of titanium halide and trialkyl aluminum component with or without other metal promoters. Alkyl aluminum halides in combination alkyl titanium esters are another example of a homogeneous catalyst used for this reaction. Low molecular weight polymers, i.e., dimers and trimers have been produced by using extremely low concentrations of these catalysts.

Similarly, free radial carbonium and carbanions have also been used to promote alpha-olefin polymerization and acid cation exchange resins have been used extensively for oligomerization, for example, U.S. Pat. Nos. 4,100,220; 4,215,011; 4,242,530; 4,232,177; 4,375,576; 4,463,211 and U.K. Patent Specification Nos. 973,555 and 2,086,415B.

Other acid catalyst for oligomerizations include sulfuric acid (U.S. Pat. Nos. 3,546,317 and 3,832,418) and perfluorosulfonic acid resin (U.S. Pat. No. 4,065,512), phosphoric acid (Ipatieff, V. N., "Catalytic Polymerization of Gaseous Olefins by Liquid Phosphoric Acid", Ing and Eng, Ch. 27, No. 9 [1935] p. 1067-1071). In the vapor phase Ipatieff observed that phosphoric acid polymerization of propylene was accelerated by the presence of butene-1 or by polymerizing butene-1 prior to propylene. The product comprises primarily $C_9$ and higher polymers. It was also found that butene-2 and isobutene had the same effect.

It is an advantage of the present invention that a liquid phase reaction may be carried out to oligomerize propylene in improved conversion from low value mixed $C_3$-$C_4$ streams.

SUMMARY OF THE INVENTION

The present invention is a process for oligomerization of propylene in a hydrocarbon feed stream comprising contacting said feed stream containing propylene and at least 5 weight % isobutene based on said feed stream in liquid phase with an acidic cation exchange resin at temperatures in the range of 80°-130° C. at LHSV in the range of 2 to 5 and recovering a product stream containing oligomers which essentially comprise $C_6$-$C_8$ mono olefins and unreacted material.

In the absence of isobutene the propylene is substantially unreactive. When the requisite amount of isobutene is present the product will be oligomers and copolymers of propylene, isobutene, and any n-butenes present. Isobutene is the most reactive component of a $C_3/C_4$ stream, hence the upper amount of isobutene present in the feed stream is about 30 weight percent. It would be desirable to react a stream containing larger amounts of isobutene with methanol to produce methyl tertiary butyl ether, which as a gasoline octane improver is more valuable. The oligomer product of the present invention is also useful as a blending material for gasolines. Preferably $C_3/C_4$ streams employed in the present invention contain from about 8 to 15 weight % isobutene. Preferably the process is carried out at temperatures in the range of 90° to 110° C.

DETAILED DESCRIPTION OF THE INVENTION

Catalytic cracker offgas (feed to the alkylator) in some refineries is out of balance, producing too much offgas for proper alkylator operation. This is especially the case where heavier feedstocks lead to greater volumes of catalytic cracker offgas.

Typically light olefins in catalytic cracker offgas are contained in a mixture of propane, propylene, isobutane, isobutene and n-butenes in a weight ratio of 10:35:30:7:20. Butenes have competitive use as alkylation feedstock and direct blendings into gasoline to improve octane performance. Thus the entire stream may be used as a feed for the present process or since isobutene is the most volatile of butenes, a separation made to recover all of the $C_3$ and enriched in isobutene in the $C_3/C_4$ fraction. Generally the gas stream used in the present process is a mixed $C_3/C_4$ hydrocarbon stream which may contain 0 to 60 wt. % propane, 5 to 90 wt. % propylene, 0 to 60 wt. % isobutane, 0 to 60 wt. % n-butane, 0 to 60 wt. % n-butenes and 5 to 30 wt. % isobutene. Preferably the total $C_4$'s in the stream comprise only about 10 to 60% of the stream with isobutene being present in the range of 8 to 15 wt. % and propylene comprising 10 to 80 wt. % of the stream.

In oligomerization according to the present invention, not only does the isobutene oligomerize substantially completely with the formation of octenes, but also branched heptenes and hexenes are formed. Propylene in the absence of isobutene is quite unreactive and requires 900 psi pressure to maintain it in liquid phase at 100° C., at which temperature conversions are less than 3%. At higher temperatures higher pressures are required and conversions are still below 10%. The oligomer product is mainly nonenes, which were not high octane components, and are not of preferred volatility. However, even in the presence of isobutene as described the conversion of propylene to oligomers is 15% at lower temperatures and pressures, with the product being substantially entirely octenes, heptenes and hexenes which all have high octane numbers.

In the presence of isobutene, propylene conversions exceed 10% at lower pressures, e.g., 600 psi and below 100° C. and as noted above the oligomer is primarily $C_6$ to $C_8$ mono olefins. More specifically over 90 wt. %, i.e., substantially all of the oligomer product is less than $C_8$ with nonenes and higher being negligible. N-butenes are not detrimental to the present process and are relatively unreactive at preferred temperatures of 90°-100°

C. Further, isobutene is preferred because a cut can be made incorporating the isobutene with propylene, while leaving the n-butenes with the pentenes for alkylation feedstock.

The pressure of the present reaction system is not critical, however it must be sufficient to maintain the reactants in liquid phase during the reaction and as set out above, the presence of the isobutene (and other C$_4$'s) reduces the pressure required to maintain the liquid phase.

The catalysts useful for the present invention are preferably in the macroreticular form which has surface areas of from 20 to 600 square meters per gram. Catalysts suitable for the present process preferably are cation exchangers, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A variety of methods may be used for preparing these polymers; for example, polymerization alone or in admixture with other monovinyl compounds, or by crosslinking with polyvinyl compounds; for example, with divinyl benzenes, divinyl toluenes, divinylphenylethers and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfonic acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contains sulfur trioxide. The treatment with fuming sulfuric acid is preferably carried out at 0° to 150° C., and the sulfuric acid should contain unreacted sulfur trioxide after the reaction. The resulting products preferably contain an average of 1.3 to 1.8 sulfonic acid groups per aromatic nucleus. Particularly, suitable polymers which contain sulfonic acid groups and are copolymers of aromatic monovinyl compounds with aromatic polyvinyl compounds, particularly divinyl compounds, in which the polyvinyl benzene content is preferably 1 to 20% by weight of the copolymer (see, for example, German Patent Specification No. 908,247).

Thermally stabilized acidic cation exchange resins may also be employed. Varying degrees of stabilization have been obtained by the incorporation of electron withdrawing groups, particularly halogens, such as bromine and chlorine into the resin polymer. U.S. Pat. Nos. 3,256,250; 3,342,755; 4,269,943 and British Pat. No. 1,393,594 describe several such procedures.

A preferred stabilized catalyst of this type is that described in U.S. Pat. No. 4,269,943, wherein chlorine or bromine are added to the polymer prior to sulfonation. In this manner the halogen is attached to the aromatic nuclei of the resin polymer. A particularly preferred form of this catalyst is the chlorine stabilized catalyst.

The thermal stability may also be obtained by attachment of —SO$_3$H groups at the para position to the divinyl benzene and ethylstyrene units (the ethyl and/or vinyl groups being attached in the meta position relative to each other). This is discussed in an article by Leonardus Petrus, Elze J. Stamhuls and Geert E. J. Joosten, "Thermal Deactivation of Strong-Acid Ion-Exchange Resins in Water", Ind Eng. Chem. Prod. Res. Dev. 1981, 20, pages 366–377.

The ion exchange resin is preferably used in a granular size of about 0.25 to 2 mm, although particles from 0.15 mm up to about 2 mm may be employed. The finer catalysts provide high surface area, but also result in high pressure drops through the reactor. The increased pressure drop as a result of the smaller granular size, may be offset by using shorter reactor tubes, i.e., from about 2 to 4 ft. long. However, catalyst particles of the preferred size and substantially free of fines are not subject to the large pressure drops. The preferred granular size is 15 to 40 mesh (approximately 0.420 to 1.3 mm), which is substantially free of fines. At the LHSV's of the present invention the preferred granular size can be used in longer tubes, i.e., six to seven feet without excessive pressure drops, i.e., less than 50 psig.

The life of the catalyst can also be adversely affected by catalyst poisons. The feed to the reactor should be free of any poisons, which include cations, particularly metals, and amines.

The catalyst is employed in a fixed bed with a flow of hydrocarbon stream therethrough. The fixed bed may be in a single continuous bed with heat exchange means located therein or more preferable the reactor is a tubular reactor wherein a plurality of tubes of ⅛ to 2 inches outside diameter are mounted in a shell. The catalyst is loaded in the tubes and heat exchange medium at the desired temperatures passes through the shell and around the tubes.

Various feed compositions utilized in the present process have produced polymer gasoline (after debutanizing) of very good octane number for use in blending or as a gasoline stock per se, e.g., RON of 101.5 and MON of 82.8 and RVP of 1.7 psi.

The following examples are intended to illustrate the invention and not to limit its scope.

EXAMPLE 1

A charge (100 cc) of fresh methanol wetted acidic cation exchange resin (Rohm and Haas Amberlyst 252-H, macroreticular resin of sulfonated styrene divinyl benzene copolymer) was loaded into a ½ inch diameter jacketed and essentially isothermal reactor. The feed tank was pressured to 180 psig with nitrogen. Liquid feed was pumped with a Milton Roy mini-pump downflow through the catalyst bed. The reactor temperature was maintained by circulating heated silicone oil through the reactor's jacket. The pressure of the reaction was maintained by a back-pressure regulator.

The length of ½ inch tubing to contain 100 cc of catalyst is 636 cm. The reaction product was collected in a high pressure collector, and transferred through a septum cap into tared, capped weighing bottles cilled in a dry ice/acetone bath at −90° C. containing ethyl benzene which reduces the vapor pressure of the propylene and prevents losses. The sample while cold (−90° C.) is analyzed by gas chromatograph.

Methanol-wetted 252-H resin was charged to the reactor, and the temperature was maintained at 85° C., 3 LHSV and 500 psig while methanol was pumped for 17 hours over the catalyst. The feed to the reactor was then changed.

The resin was stabilized by operating at bath/bed exotherm temperatures of 94°/94° C. (Run A), 94°/107° C. (Run B), and 96°/110° C. (Run C) on feeds as specified in TABLE I, at 700 psig and an LHSV of 3. The results are set out in TABLE I. Percents are by weight. The results show increases of propylene conversion from 1% to 26% where isobutene is present.

TABLE I

| RUN | A | B | C |
|---|---|---|---|
| FEED | | | |
| Propylene | 70 | 70 | 29 |
| N—butane | 30 | — | 38 |
| Isobutene | — | 30 | 12 |
| N—butene | — | — | 21 |
| PRODUCT | | | |
| % Conversion | | | |
| Propylene | 1 | 8 | 26 |
| N—butane | 0 | — | 0 |
| Isobutene | — | 92 | 100 |
| N—butene | — | — | 15 |
| % Selectivity to Oligomer | | | |
| Propylene | 100 | 100 | 100 |
| Isobutene | — | 100 | 100 |
| N—butene | — | — | 100 |

EXAMPLE 2

In another run with a feed of 75 wt. % propylene and 25 wt. % isobutene (3:1 wt. ratio) carried out in the equipment described in Example 1, at bath/exotherm temperature of 94°/105° C., LHSV 3 produced propylene conversion of about 15% and total olefin conversion of about 45% with the oligomer product distribution being 5% hexene, 13% heptene and 82% octene. The RON, MON and RVP for the debutanized reactor effluent was 101.5, 82.8 and 1.7 psig respectively.

The invention claimed is:

1. A process for the oligomerization of propylene in a hydrocarbon feed stream comprising contacting said feed stream containing propylene and at least 5 weight % isobutene based on said feed stream in liquid phase with an acidic cation exchange resin at temperatures in the range of 80°-130° C. at LHSV in the range of 2 to 5 and recovering a product stream containing oligomers, comprising primarily $C_6$ to $C_8$ mono olefins, and unreacted material.

2. The process according to claim 1 wherein up to 30 weight % isobutene is present in said feed stream.

3. The process according to claim 1 wherein from about 8 to 15 wt. % isobutene is present in said feed stream.

4. The process according to claim 1 wherein said feed stream is a $C_3/C_4$ hydrocarbon stream.

5. The process according to claim 4 wherein said feed stream contains propane, propylene, butane, n-butene, isobutane and isobutene.

6. The process according to claim 5 wherein said feed stream contains 0 to 60 wt. % propane, 5 to 90 wt. % propylene, 0 to 60 wt. % butane, 0 to 60 wt. % n-butenes, 0 to 60 wt. % isobutane and 5 to 30 wt. % isobutene.

7. The process according to claim 1 wherein the temperature is in the range of 90° to 110° C.

8. The process according to claim 1 wherein said feed stream contains from 5 to 90 wt. % propylene.

9. The process according to claim 1 wherein said oligomers in said product stream are comprised of over 90 wt. % $C_6$ to $C_8$ mono olefins.

10. The process according to claim 9 wherein said oligomers in said product stream are comprised of substantially all $C_6$ to $C_8$ mono olefins.

11. A process for oligomerization of propylene in a $C_3/C_4$ hydrocarbon feed stream comprising contacting said feed stream containing from about 8 to 15 wt. % isobutene based on said feed stream in liquid phase with an acidic cation exchange resin at temperatures in the range of 80° to 120° C. at LHSV of 2 to 5 and recovering a product stream containing oligomers, comprised of over 90 wt. % $C_6$ to $C_8$ mono olefins and unreacted material.

12. The process according to claim 11 wherein said oligomers in said product stream are substantially all $C_6$ to $C_8$ mono olefins.

* * * * *